United States Patent

Hu et al.

[11] Patent Number: 5,963,614
[45] Date of Patent: Oct. 5, 1999

[54] FILTERS FOR SINGLE SLICE HELICAL IMAGE RECONSTRUCTION IN A COMPUTED TOMOGRAPHY SYSTEM

[75] Inventors: Hui Hu, Waukesha, Wis.; Yun Shen, Tokyo, Japan

[73] Assignee: General Electric Company, Milwaukee, Wis.

[21] Appl. No.: 08/977,440

[22] Filed: Nov. 26, 1997

[51] Int. Cl.$^6$ .................................................... A61B 6/03
[52] U.S. Cl. ................................ 378/15; 378/4; 378/901
[58] Field of Search .................................. 378/4, 15, 901

[56] References Cited

U.S. PATENT DOCUMENTS 5,430,783  7/1995  Hu et al. .................................... 378/15

*Primary Examiner*—David Vernon Bruce
*Attorney, Agent, or Firm*—John S. Beulick; Christian G. Cabou; Phyllis Y. Price

[57] ABSTRACT

Filtering algorithms which offer tradeoffs between slice profile widening and the noise and mAs, reduction are described. In one embodiment, the FWHM is adjusted based on the helical pitch to provide a constant reduction of noise. The percentage increase of FWHM is a function of helical pitch as described below in more detail. The amount of projection data used to reconstruct an image is fixed, independent of the helical pitch. In another embodiment, a roughly constant percentage increase of FWHM is maintained while the amount of reduction of mAs or noise decreases as helical pitch increases. The amount of projection data used to reconstruct an image is also a function of helical pitches. The above described filters provide that for various helical pitches, the filter maintains the same amount of mAs or noise reduction, or maintains the same percentage increase of FWHM. Such filters can be implemented without significantly increasing the processing time.

8 Claims, 2 Drawing Sheets

FILTERS FOR SINGLE SLICE HELICAL IMAGE RECONSTRUCTION IN A COMPUTED TOMOGRAPHY SYSTEM

FIELD OF THE INVENTION

This invention relates generally to computed tomography (CT) imaging and more particularly, to image reconstruction using data collected by a CT system in a single slice helical scan.

BACKGROUND OF THE INVENTION

In at least one known single slice CT system configuration, an x-ray source projects a fan-shaped beam which is collimated to lie within an X-Y plane of a Cartesian coordinate system and generally referred to as the "imaging plane". The x-ray beam passes through the object being imaged, such as a patient. The beam, after being attenuated by the object, impinges upon a one row array of radiation detectors. The intensity of the attenuated beam radiation received at the detector array is dependent upon the attenuation of the x-ray beam by the object. Each detector element of the array produces a separate electrical signal that is a measurement of the beam attenuation at the detector location. The attenuation measurements from all the detectors are acquired separately to produce a transmission profile.

In known third generation CT systems, the x-ray source and the detector array are rotated with a gantry within the imaging plane and around the object to be imaged so that the angle at which the x-ray beam intersects the object constantly changes. A group of x-ray attenuation measurements, i.e., projection data, from the detector array at one gantry angle is referred to as a "view". A "scan" of the object comprises a set of views made at different gantry angles during one revolution of the x-ray source and detector.

In an axial scan, the projection data is processed to construct an image that corresponds to a two dimensional slice taken through the object. One method for reconstructing an image from a set of projection data is referred to in the art as the filtered back projection technique. This process converts that attenuation measurements from a scan into integers called "CT numbers" or "Hounsfield units", which are used to control the brightness of a corresponding pixel on a cathode ray tube display.

To reduce the total scan time, a "helical" scan may be performed. To perform a "helical" scan, the patient is moved while the data for the prescribed volume coverage is acquired. Such a system generates a single helix from a one fan beam helical scan. The helix mapped out by the fan beam yields projection data from which images in each prescribed slice may be reconstructed.

Reconstruction algorithms for helical scanning typically use helical weighting algorithms which weight the collected data as a function of view angle and detector channel index. Specifically, prior to filtered back projection, the data is weighted according to a helical weighting factor, which is a function of both the gantry angle and detector angle. Although the known algorithms generate compact slice profiles, some noticeable artifacts may be generated in the reconstructed image. Furthermore, these algorithms result in increases of total radiation dosage to the patient and/or the noise in the reconstructed images.

It would be desirable to provide a method which provides a selectable tradeoff of the compact slice profile for reduced artifacts, noise, and patient dose. Furthermore, it would be desirable to provide a flexible algorithm so that for various helical pitches, it either maintains the same amount of mAs or noise reduction, or maintains the same percentage increase of the image full width at half maximum (FWHM). It also would be desirable to provide an algorithm which facilitates performing these tasks without significantly increasing the processing time.

SUMMARY OF THE INVENTION

These and other objects may be attained in a CT system configured to perform a single slice helical scan, which includes a projection domain z filtering algorithm that generates a modified weighting factor. More particularly, and with respect to generating the modified weighting factor, a helical reconstruction algorithm weighting factor is shifted in the view angle direction and averaged to generate the modified weighting factor. Examples of image reconstruction algorithms which may be utilized in reconstructing an image from data obtained in a helical scan are described in Crawford and King, "Computed Tomography Scanning With Simultaneous Patient Translation", Med. Phys. 17(6), 967–982, 1990.

In one embodiment, the helical weighting factor is modified according to gantry angle ($\beta$), detector angle ($\gamma$), and a filter kernel (h(i)) in accordance with the following:

$$W_f(\beta, \gamma) = \sum_{i=-n}^{i=n} h(i) W(\beta - i\Delta\beta, \gamma)$$

where:

$\gamma$ is the detector angle;

$\beta$ is the gantry angle;

$W(\beta,\gamma)$ is the original weighting coefficient generated by the helical reconstruction algorithm;

$\Delta\beta$ is the shift along the view angle direction; and h(i) is the weighting applied to the i th shifted version.

The filter kernel (h(i)) can be selected, as described hereinafter, to provide image smoothing, i.e., reduce noise and image artifacts, or to increase image "sharpness". The modified weighting factor is thus a shifted and weighted average version of the original weighting factor.

The image full width at half maximum (FWHM) may be adjusted based on the helical pitch to provide a constant reduction of noise. The percentage increase of FWHM is a function of helical pitch as described below in more detail. The amount of projection data used to reconstruct an image is fixed, independent of the helical pitch. Alternatively, a roughly constant percentage increase of FWHM is maintained while the amount of reduction of mAs or noise decreases as helical pitch increases. With this alternative, the amount of projection data used to reconstruct an image is also a function of helical pitches.

The above described filters provide that for various helical pitches, the filter maintains the same amount of mAs or noise reduction, or maintains the same percentage increase of FWHM. Such filters also facilitate reducing artifacts and do not significantly increase the processing time.

DETAILED DESCRIPTION

Figure 1:
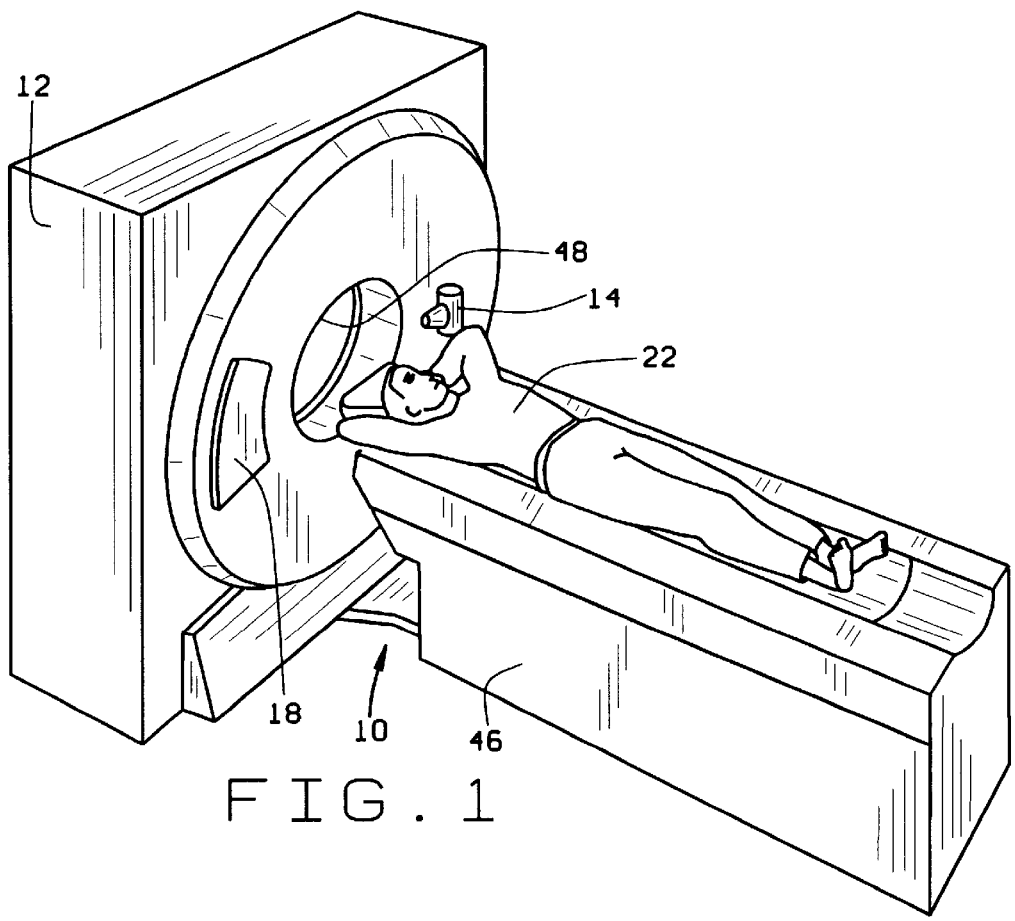
FIG. 1 is a pictorial view of a CT imaging system.
Figure 2:
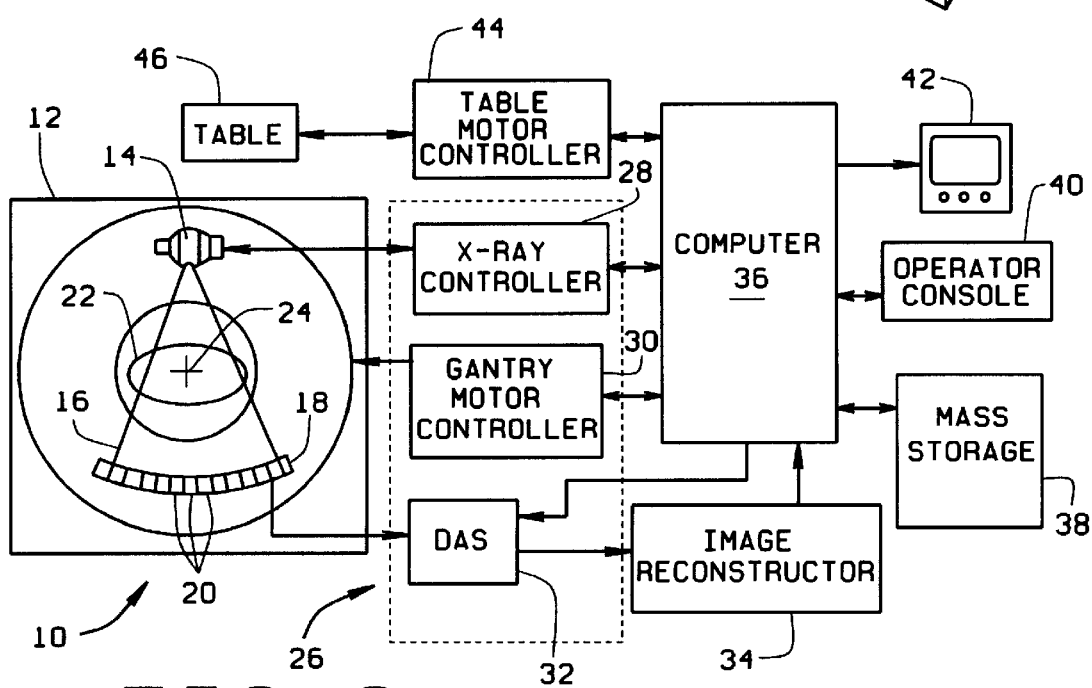
FIG. 2 is a block schematic diagram of the system illustrated in FIG. 1.

Referring to FIGS. 1 and 2, a single slice computed tomography (CT) imaging system 10 is shown as including a gantry 12 representative of a "third generation" CT scanner. Gantry 12 has an x-ray source 14 that projects a beam of x-rays 16 toward a detector array 18 on the opposite side of gantry 12. Detector array 18 is formed by one row of detector elements 20 which together sense the projected x-rays that pass through a medical patient 22. Each detector element 20 produces an electrical signal that represents the intensity of an impinging x-ray beam and hence the attenuation of the beam as it passes through patient 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high speed image reconstruction. The reconstructed image is applied as an input to a computer 36 which stores the image in a mass storage device 38.

Computer 36 also receives commands and scanning parameters from an operator via console 40 that has a keyboard. An associated display device 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 in gantry 12. Particularly, table 46 moves portions of patient 22 through gantry opening 48.

The known helical reconstruction algorithms may generally be classified as Helical Extrapolative (HE) or Helical Interpolative (HI) algorithms. These algorithms typically apply a weighting factor to the projection data in order to reconstruct an image. This weighting factor is generally based on both the fan angle and view angle.

Each image generated with a helical reconstruction algorithm, as described above, corresponds to a two dimensional slice taken through patient 22. Each image typically includes projection data acquired during only one rotation of gantry 12, or 2 π worth of data. As explained above, such generated images may have artifacts and noise, particularly at the beginning and end of a rotation, i.e., $\beta=0$ or $\beta=2\pi$.

The following discussion of filtering algorithms and image quality sometimes refers specifically to projection data. The filtering algorithms, however, are not limited to practice in connection with such protection data and may be used with image data. Moreover, the algorithms are not directed to any particular helical image reconstruction algorithm. Rather, the filtering algorithms may be used in conjunction with many different types of helical reconstruction algorithms. Further, in one embodiment, the filtering would be implemented in computer 36 which would process, for example, data stored in mass storage 38. Many other alternative implementations are, of course, possible.

As one specific example, in a single slice system with one row of detectors, a helical reconstruction algorithm to be applied to projection data during reconstruction includes a weighting factor $W(\beta,\gamma)$ accorded to each gantry angle ($\beta$) and detector angle ($\gamma$). In accordance with the present invention, the modified weighting factor $W_f(\beta,\gamma)$ is:

$$W_f(\beta, \gamma) = \sum_{i=-n}^{i=n} h(i)W(\beta - i\Delta\beta, \gamma)$$

where:

$\gamma$ is the detector angle;

$\beta$ is the gantry angle;

$W(\beta,\gamma)$ is the weighting coefficient, applied or pursuant to, a helical reconstruction algorithm;

$\Delta\beta$ is the shift along the view angle direction; and h(i) is the weighting applied to the i th shifted version.

This modified weighting factor $W_f(\beta,\gamma)$ is a shifted and weighted average version of the helical weighting function. The kernel length is 2n+1 terms. In most cases, n=1, or 3 terms, is sufficient. The modified weighting factor $W_f(\beta,\gamma)$ is applied to the projection data to generate z-averaged slices. More than one rotation, i.e., more than 2 π, worth of data is used to generate the z-average slices. By utilizing more than one rotation worth of data, discontinuities can be "smoothed" without significantly increasing the slice width.

In known single slice helical reconstruction, the slice profiles and image noises of reconstructed images are primarily determined by x-ray collimation, the patient-feeding speed, the x-ray tube output, and the weighting function $W(\beta,\gamma)$. In the present invention, and in addition to the foregoing, the filter kernel h(i) also affects slice profiles and image noises. Particularly, if filter kernel h(i) is (1,1,1), then image artifacts and noise are reduced, i.e., the image is "smoothed". Accordingly, by selecting the filter kernel h(i), tradeoffs between slice profile and image noise can be made.

The profile width of the resulting z-averaged slice is related to both the intrinsic slice profile, i.e., the original slice profile without any z filtering, and the filter kernel. The region of the filter kernel is represented by $2n\Delta\beta$. The detailed shape of the profile of the resulting slice is also affected by kernel h(i). Accordingly, and in contrast to known algorithms, the resulting slice profile width can be broader than the intrinsic slice profile width. Therefore, image noise is reduced. In addition, it is believed that the x-ray tube output required for satisfactory image generation may be reduced.

In one embodiment of the present invention, the FWHM is adjusted based on the helical pitch to provide a constant reduction of noise. Specifically, the percentage increase of FWHM is a function of helical pitch, as set forth below in Table I. The amount of projection data used to reconstruct an image is fixed, independent of the helical pitch.

TABLE I

| helical pitch | FWHM of HE (normalized to the collimation) | FWHM of Helical + (normalized to that of HE) | # of rotation |
|---|---|---|---|
| 0.25 | 1.00 | 1.00 | 1.6 |
| 0.50 | 1.00 | 1.00 | 1.6 |
| 0.75 | 1.00 | 1.02 | 1.6 |
| 1.00 | 1.00 | 1.10 | 1.6 |
| 1.25 | 1.03 | 1.22 | 1.6 |
| 1.50 | 1.09 | 1.33 | 1.6 |
| 1.75 | 1.17 | 1.43 | 1.6 |
| 2.00 | 1.27 | 1.50 | 1.6 |
| 2.25 | 1.38 | 1.53 | 1.6 |
| 2.50 | 1.50 | 1.55 | 1.6 |
| 2.75 | 1.63 | 1.56 | 1.6 |
| 3.00 | 1.75 | 1.57 | 1.6 |

Figure 3:
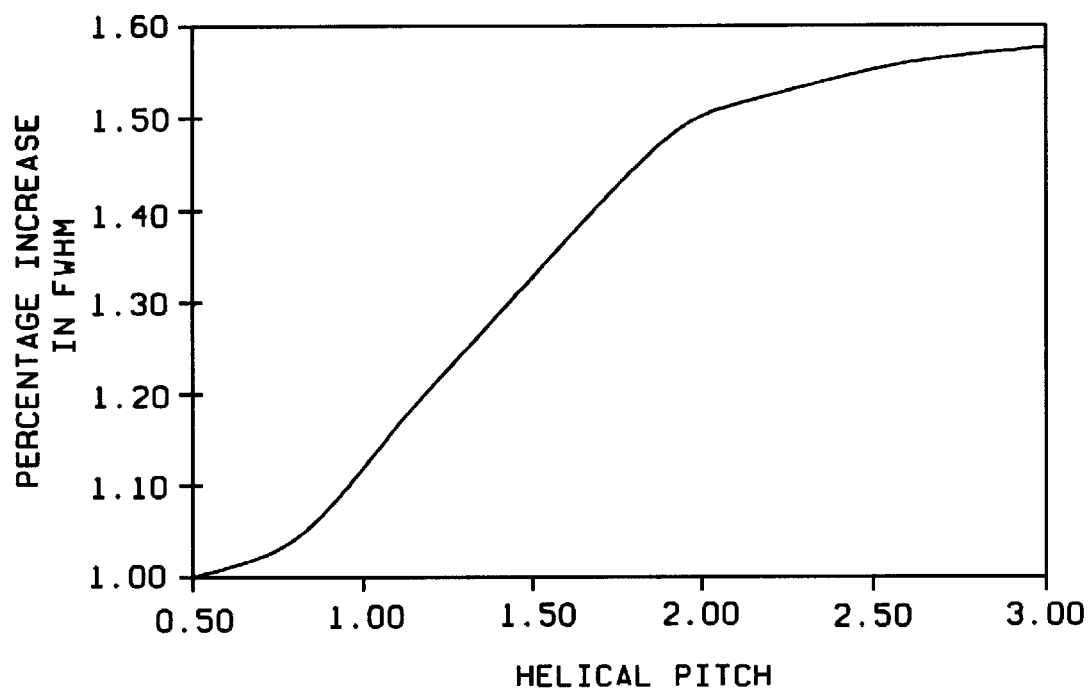
FIG. 3 is a plot illustrating percentage increase of FWHM relative to helical pitch in accordance with one embodiment of the present invention.

The percentage increase of FWHM (relative to that of HE reconstruction of the corresponding pitch) is listed in the 3rd column of Table I and is plotted in FIG. 3 as a function of helical pitch.

The percentage increase in FWHM, as shown in FIG. 3 and in Table I, is relative to the FWHM of the HE reconstruction at the corresponding helical pitch and collimation. For example, with a 5 mm collimation and for 1:1 pitch helical CT, a 37% reduction in mAs is achieved with a 10% widening of FWHM (from 5 mm to 5.5 mm). However, for 1.5:1 pitch helical CT, the same amount of reduction in mAs is achieved with a 33% widening of FWHM (from 5.45 mm to 7.25 mm). In this example, 1.6 rotation worth of projection data is used to reconstruct an image, independent of the helical pitch.

In another embodiment, a roughly constant percentage increase of FWHM is maintained while the amount of reduction of mAs or noise decreases as helical pitch increases. The amount of projection data used to reconstruct an image is also a function of helical pitches.

Figure 4:
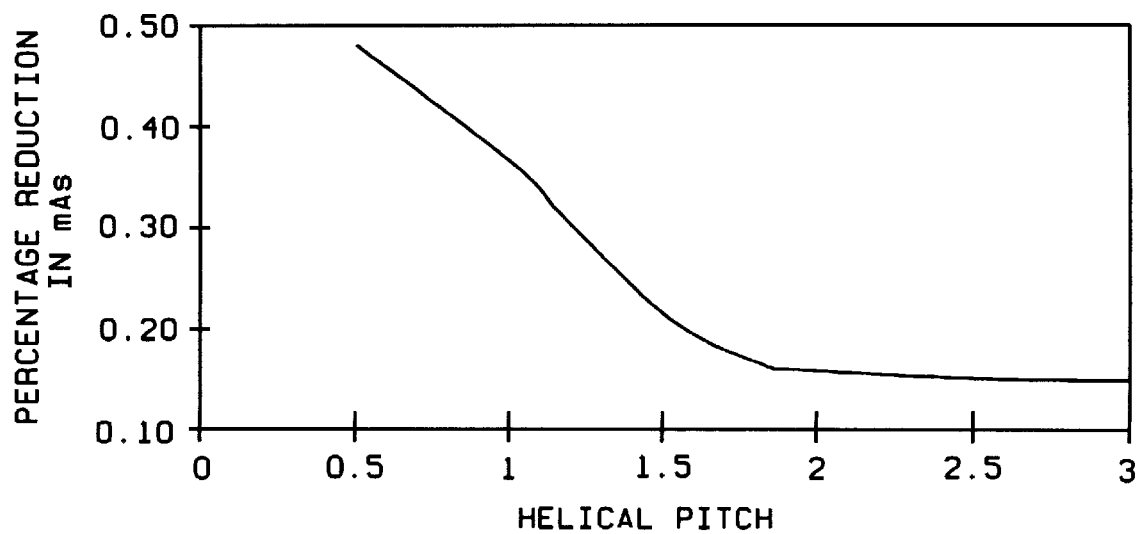
FIG. 4 is a plot illustrating helical pitch relative to a percentage reduction in mAs in accordance with another embodiment of the present invention.

For example, for the filter to maintain a roughly 10% increase of FWHM for helical pitch from 1 to 3, the mAs reduction is listed in the 4th column of Table II and is plotted in FIG. 4 as a function of helical pitches. The variations in FWHM and the amount of projection data required to reconstruct an image are also listed in the 3rd and 5th columns in Table II.

TABLE II

| helical pitch | FWHM of HE (normalized to the collimation) | FWHM of Helical + (normalized to that of HE) | Percentage reduction in mAs | # of rotation |
|---|---|---|---|---|
| 0.50 | 1.00 | 1.00 | 0.49 | 1.81 |
| 1.00 | 1.00 | 1.101 | 0.37 | 1.60 |
| 1.25 | 1.03 | 1.128 | 0.28 | 1.48 |
| 1.50 | 1.09 | 1.125 | 0.21 | 1.39 |
| 1.75 | 1.17 | 1.118 | 0.17 | 1.34 |
| 2.00 | 1.27 | 1.118 | 0.16 | 1.32 |
| 3.00 | 1.75 | 1.12 | 0.15 | 1.31 |

The filter is a function of helical pitch, which can be approximated by curve-fitting a set of predefined points. These points are listed in Table III and the function is:

$$\Delta\beta = 2\pi(a0 + a1p + a2p^2 + a3p^3 + a4p^4 + a5p^5)$$

where, $\Delta\beta$ is the angular shift, p is the helical pitch, and a is a set of coefficients derived from the curve-fitting. Values for a are given in Table IV. A simple three point kernel (h=[1, 1,1]) is sufficient for curve fitting. The amount of projection data used to reconstruct an image can be computed as $1 + 2*\Delta\beta/2\pi$ rotation, which is also a function of helical pitches.

TABLE III

| helical pitch | 0.30 | 0.70 | 1.00 | 1.25 | 1.50 | 1.75 | 2.00 | 2.50 | 3.00 |
|---|---|---|---|---|---|---|---|---|---|
| $\Delta\beta/2\pi$ | 0.40 | 0.37 | 0.30 | 0.24 | 0.19 | 0.17 | 0.16 | 0.16 | 0.16 |
| FWHM of Helical + (normalized to that of HE) | 1.00 | 1.02 | 1.10 | 1.12 | 1.12 | 1.12 | 1.12 | 1.12 | 1.12 |

TABLE IV

| $\alpha 0$ | 0.24922 |
|---|---|
| $\alpha 1$ | 0.90792 |
| $\alpha 2$ | -1.63913 |
| $\alpha 3$ | 1.034665 |
| $\alpha 4$ | -0.28467 |
| $\alpha 5$ | 0.029039 |

The above described filters provide that for various helical pitches, the filter maintains the same amount of mAs or noise reduction, or maintains the same percentage increase of FWHM. Such filters can be implemented without significantly increasing the processing time.

From the preceding description of various embodiments of the present invention, it is evident that the objects of the invention are attained. Although the invention has been described and illustrated in detail, it is to be clearly understood that the same is intended by way of illustration and example only and is not to be taken by way of limitation. Accordingly, the spirit and scope of the invention are to be limited only by the terms of the appended claims.

We claim:

1. A system for producing a tomographic image of an object using data acquired from a single detector row in a helical scan, said system comprising a processor programmed to:
   generate a helical weighting factor;
   generate a modified weighting factor based on the generated helical weighting factor, said modified weighting factor $W_f(\beta,\gamma)$ being:

$$W_f(\beta, \gamma) = \sum_{i=-n}^{i=n} h(i) W(\beta - i\Delta\beta, \gamma)$$

where:

$\gamma$ is the detector angle;

$\beta$ is the gantry angle;

$W(\beta,\gamma)$ is the helical weighting coefficient;

$\Delta\beta$ is the shift along the view angle direction; and $h(i)$ is the weighting applied to the i th shifted version, and wherein a substantially constant reduction of noise is provided and the image full width half maximum is a function of helical pitch; and apply the modified weighting factor to the data.

2. A system in accordance with claim 1 wherein said modified weighting factor is applied to projection data.

3. A system in accordance with claim 1 wherein said modified weighting factor is applied to image data.

4. A system for producing a tomographic image of an object using data acquired from a single detector row in a helical scan, said system comprising a processor programmed to:

generate a helical weighting factor;

generate a modified weighting factor based on the generated helical weighting factor, said modified weighting factor $W_f(\beta,\gamma)$ being:

$$W_f(\beta, \gamma) = \sum_{i=-n}^{i=n} h(i) W(\beta - i\Delta\beta, \gamma)$$

where:

$\gamma$ is the detector angle;

$\beta$ is the gantry angle;

$W(\beta,\gamma)$ is the helical weighting coefficient;

$\Delta\beta$ is the shift along the view angle direction; and $h(i)$ is the weighting applied to the i th shifted version, and wherein a constant percentage increase of the image full width half maximum is maintained and an amount of noise reduction decreases as helical pitch increases; and apply the modified weighting factor to the data.

5. A system in accordance with claim 4 wherein an amount of projection data used to reconstruct an image is a function of helical pitch.

6. A system in accordance with claim 4 wherein a constant percentage increase in FWHM is maintained by adjusting a filter as a function of helical pitch, said function being represented as:

$$\Delta\beta = 2\pi(a0 + a1p + a2p^2 + a3p^3 + a4p^4 + a5p^5)$$

where, $\Delta\beta$ is the angular shift, p is the helical pitch, and a is a set of coefficients derived from curve-fitting.

7. A system in accordance with claim 4 wherein said modified weighting factor is applied to projection data.

8. A system in accordance with claim 4 wherein said modified weighting factor is applied to image data.

* * * * *